United States Patent [19]

Will

[11] Patent Number: 4,697,703
[45] Date of Patent: Oct. 6, 1987

[54] JOINT PROSTHESIS PACKAGE

[76] Inventor: Malcolm Will, 120 Francis St., Keyport, N.J. 07735

[21] Appl. No.: 881,276

[22] Filed: Jul. 2, 1986

[51] Int. Cl.$^4$ .............................................. A61B 17/06
[52] U.S. Cl. .................................. 206/438; 206/363; 206/485; 206/525; 206/828
[58] Field of Search .............. 206/210, 363, 438, 477, 206/485, 499, 525, 828; 220/410

[56] References Cited

U.S. PATENT DOCUMENTS

| | | | |
|---|---|---|---|
| 3,365,308 | 1/1968 | Janicke | 206/525 |
| 3,476,282 | 11/1969 | Monaco et al. | 220/410 |
| 4,101,031 | 7/1978 | Cromie | 206/438 |
| 4,211,325 | 7/1980 | Wright | 206/525 |
| 4,225,045 | 9/1980 | Rayner et al. | 206/525 |
| 4,340,138 | 7/1982 | Bernhardt | 220/410 |
| 4,346,833 | 8/1982 | Bernhardt | 206/459 |
| 4,348,421 | 9/1982 | Sakakibara et al. | 220/410 |

FOREIGN PATENT DOCUMENTS 2381447 10/1978 France ............................. 206/525
331057 7/1970 Switzerland ...................... 206/525

Primary Examiner—Stephen Marcus
Assistant Examiner—David T. Fidei
Attorney, Agent, or Firm—Peter L. Klempay

[57] ABSTRACT

A package for holding a medical item such as a joint prosthesis part and maintaining the same in a double sterile state includes an inner package and lid each receiving a snap-in insert, a film cover sealing the inner package and lid combination, an outer package containing the combination and a second film cover sealing the outer package. Complementary recesses and lugs are formed on the lid and inner and outer packages to hold these units together. The inserts are provided with projections to engage and cradle the packaged item. A range of inserts is provided to permit the packaging of items of various sizes and configurations without otherwise modifying the package. Alternatively, either the inner package or the lid may include an integrally formed projection and a single insert is carried by the other one thereof.

16 Claims, 8 Drawing Figures

JOINT PROSTHESIS PACKAGE

The present invention pertains to sterile packages for medical items such as joint prostheses and, more particularly, to such packages which readily accomodate a range of sizes of such items.

BACKGROUND OF THE INVENTION

The packaging of medical items intended for use in surgury frequently involves the use of a double sterile package, that is, an inner package containing the item and being sealed and sterilized and an outer package enclosing the inner package and also being sealed and sterilized. With an item such as a hip joint prosthesis which is relatively heavy, the item must be firmly restrained against movement within the package, necessitating the use of specially configured containers. As such items are available in a wide range of sizes, for example one hip joint replacement element is available in more than seventy sizes, the provision of suitable packaging can entail considerable expense in inventory and in the obtaining of regulatory approval for the packaging.

It is the primary object of the present invention to provide a package for medical items which are provided in a range of sizes which package can be adapted to accomodate various sized items.

It is also an object of the present invention to provide such a medical item package in which a single basic package assembly need be approved and inventoried.

A further object of the present invention is the provision of such a medical item package which securely retains the packaged item and which maintains a double sterile condition.

SUMMARY OF THE INVENTION

The above and other objects of the invention which will become apparant hereinafter are achieved by the provision of a double sterile package including an inner package having bottom and side walls, inwardly projecting lugs being provided on the side walls closely adjacent the bottom walls and outwardly projecting lugs being formed on the side walls adjacent the upper ends thereof; a first insert having generally the same plan configuration as the bottom wall and adapted to be snapped into place beneath the lower lugs; an inner package lid having an outwardly projecting lip overlying, in the closed position, the upper ends of the inner container side walls, downwardly projecting side walls including outwardly projecting lugs adapted to engage the upper lugs of the inner container side walls, additional short vertical walls spaced inwardly from the downwardly projecting walls and a main top wall joining the upper ends of the additional walls, the additional walls being provided with inwardly projecting lugs spaced from the top wall; a second insert having generally the same configuration as the main top wall and adapted to be snapped into place between the additional wall lugs and the top wall; a bacterially impervious film adapted to be sealed to the lid and the inner package; an outer package having bottom and side walls and configured to closely receive the inner package, the side walls of the outer package being provided with lugs for engagement with the upper lugs of the inner package; and a second bacterially impervious film adapted to be sealed to the outer package. The two inserts of the inner package are provided with suitable projections and/or recesses for closely cradling the medical item and are the only elements of the package assembly which need to be varied to accomodate a range of item sizes. In an alternate construction, either the inner container or the lid has a projection formed integrally therein and the other of these two package components carries an insert. Preferrably, the packages, inserts and lid are formed of thermoformed plastic materials.

For a more complete understanding of the invention and the objects and advantages thereof, reference should be had to the accompanying drawings and the following detailed description wherein a preferred embodiment of the invention is illustrated and described.

DESCRIPTION OF THE PREFERRED EMBODIMENT

Figure 1A:
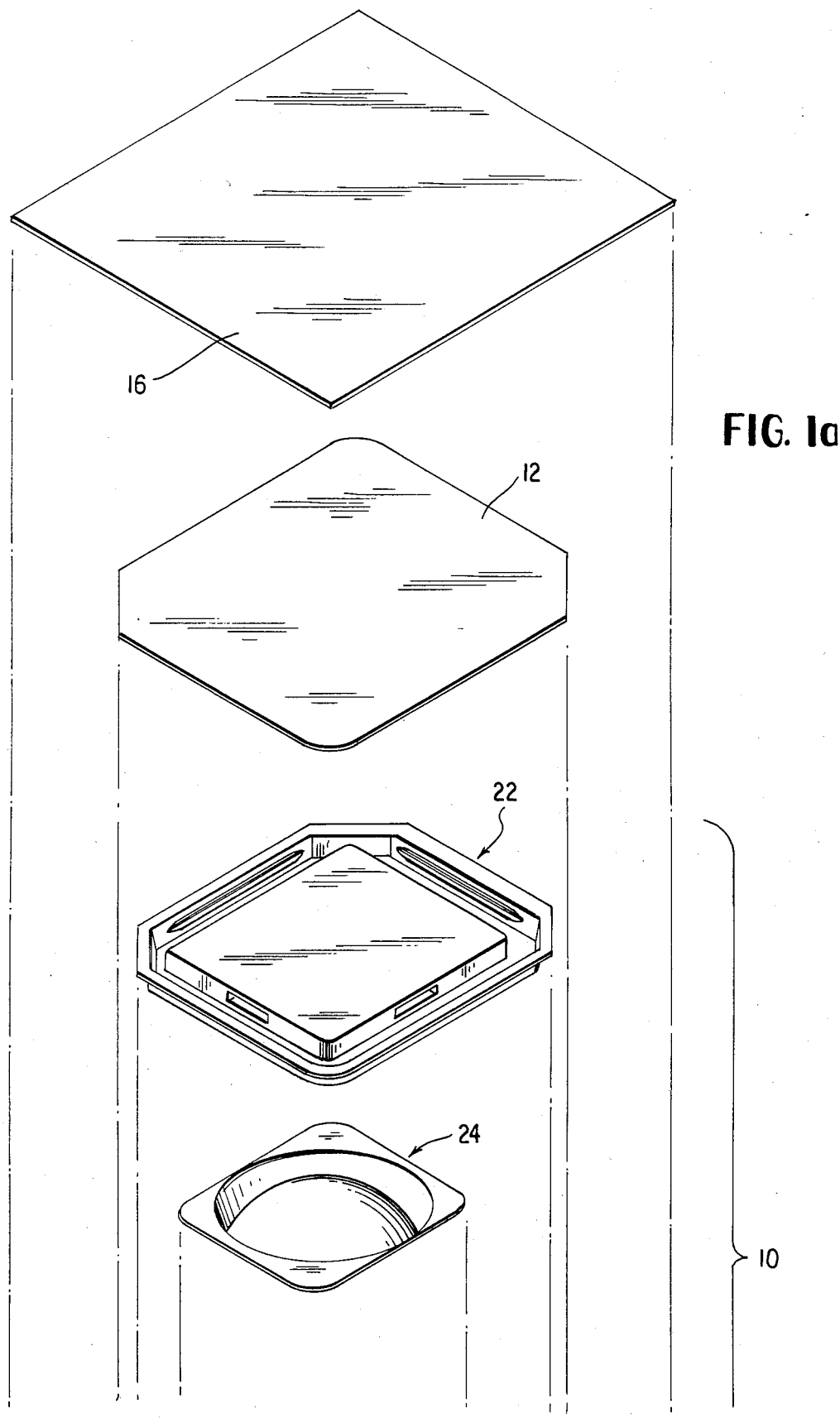
FIGS. 1a and 1b together provide an exploded perspective view of the package of the present invention.
Figure 1B:
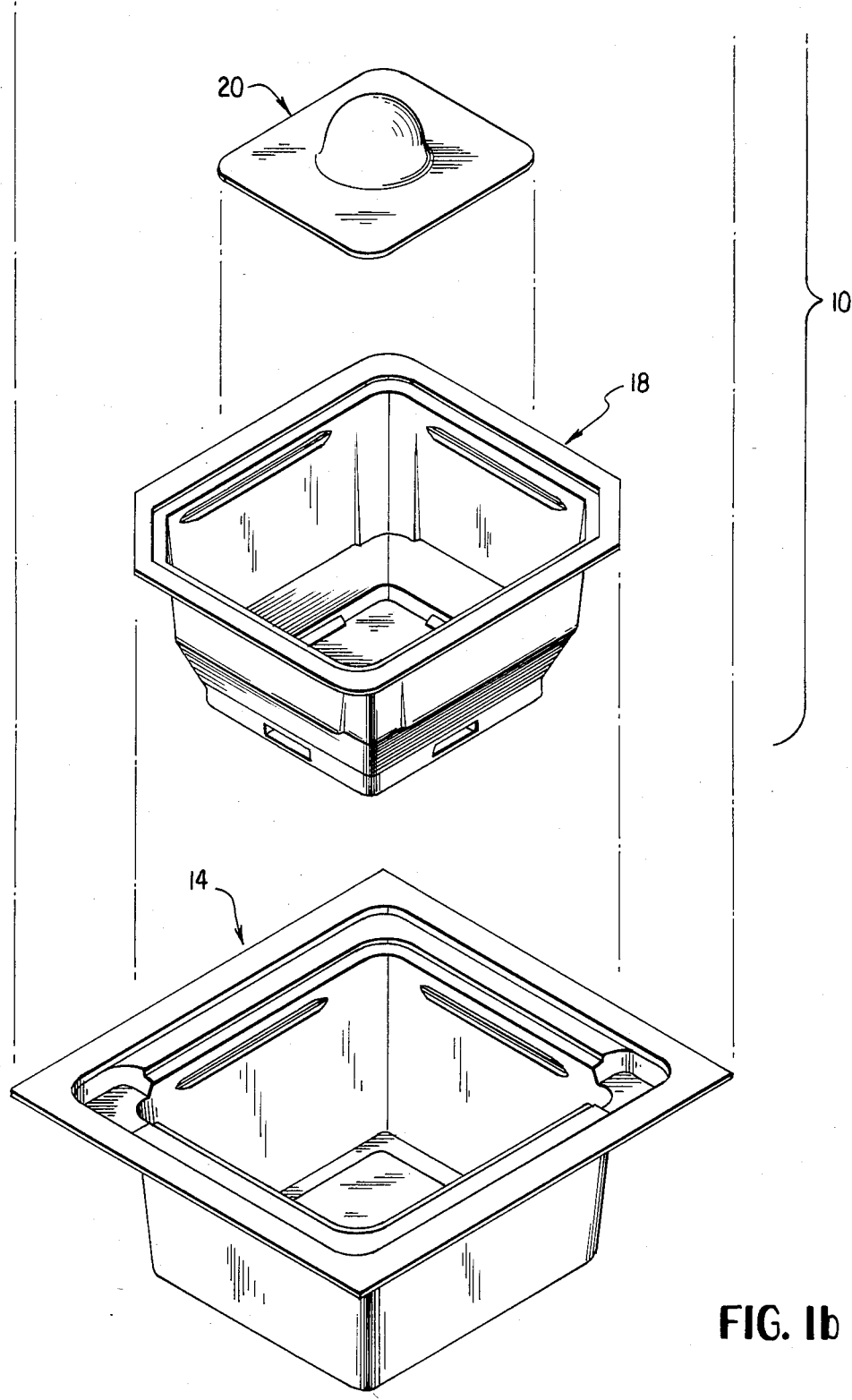
Figure 2:
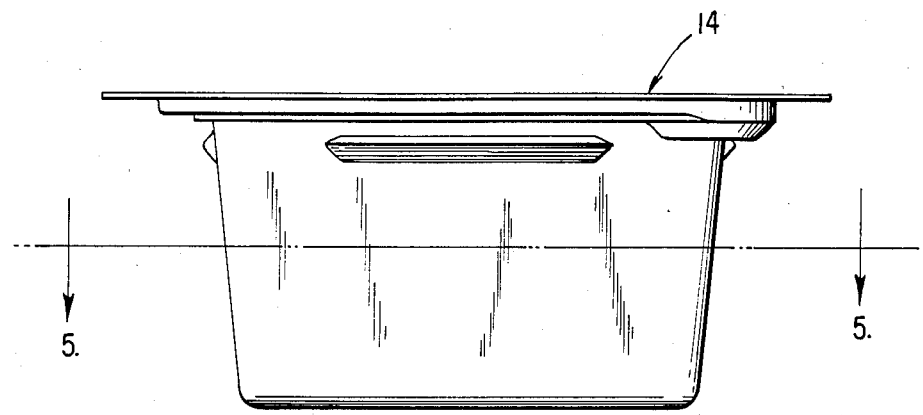
FIG. 2 is a side elevational view of the package.

The package of the present invention is a double sterile package intended to contain an item such as a hip joint replacement prosthesis. As is shown in FIG. 1, the package includes an inner package assembly designated generally by the reference numeral 10 and provided with a sealing cover 12 and an outer package designated generally by the reference numeral 14, also provided with a sealing cover 16.

The inner package assembly consists of an open-top container 18, a first insert 20 contained therein, a lid 22 and a second insert 24 carried by the lid. Container 18 has a bottom wall 26, preferably of rectangular plan configuration, side walls 28, 30, 32 and 34 and, at the upper ends of the side walls, an outwardly projecting lip 36. The principal portion of each of the side walls has the same cross sectional configuration including a lower vertical wall section 38 joined to and extending upwardly by a short distance from the bottom wall 26, an intermediate wall section 40 diverging outwardly at, for example, a 45° angle, and an upper wall section 42 also diverging outwardly but at a shallow angle relative to the vertical. Each of the lower wall sections includes a lug 44 generally longitudinally centered thereon and projecting inwardly in closely spaced relation to the bottom wall 26. Closely adjacent the upper end of each of the upper wall sections 42 an outwardly projecting lug 46 is provided, each lug 46 being of V-shaped cross sectional configuration with an inclined lower surface 48 and a substantially horizontal upper surface 50. It will be noted that, for each lug, a corresponding recess 51 is formed on the opposite face of the wall. The lip 36 is of stepped configuration, having a first horizontal zone 52 extending outwardly from the perimeter of the side walls and a second, outer horizontal zone 54 spaced upwardly from the first zone by a distance substantially equal to the wall thickness. Completing the description of the container 18, it will be noted that two opposite corners thereof, for example, those formed by the intersections of walls 30 and 32 and of walls 34 and 36, are rounded while the remaining corners include angled wall portions.

Figure 3:
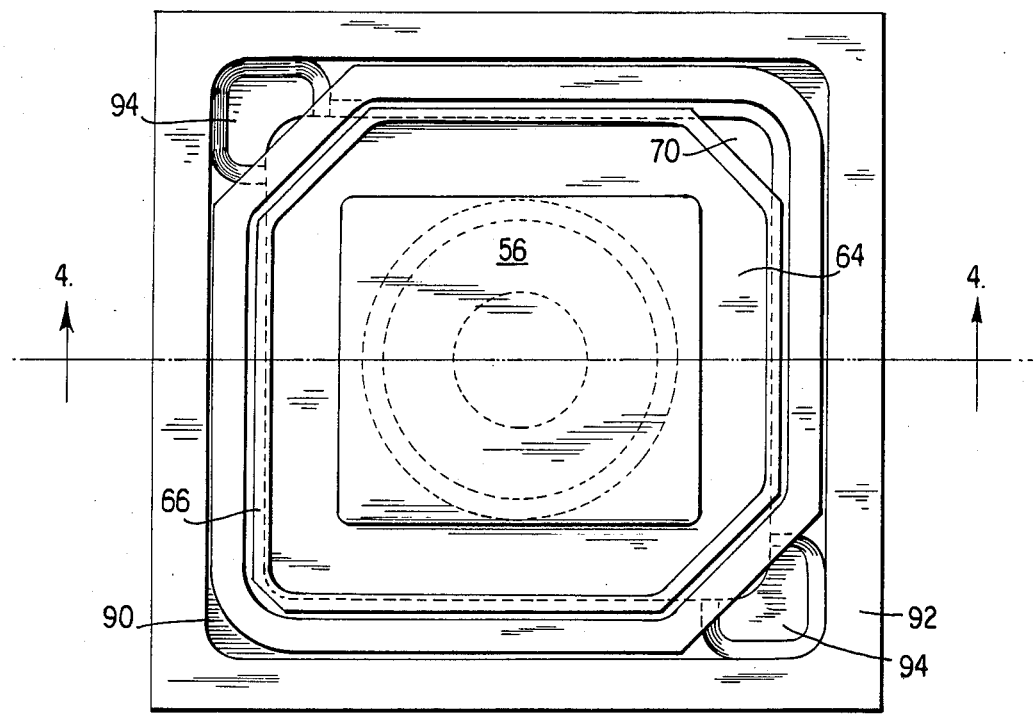
FIG. 3 is a top plan view thereof.
Figure 4:
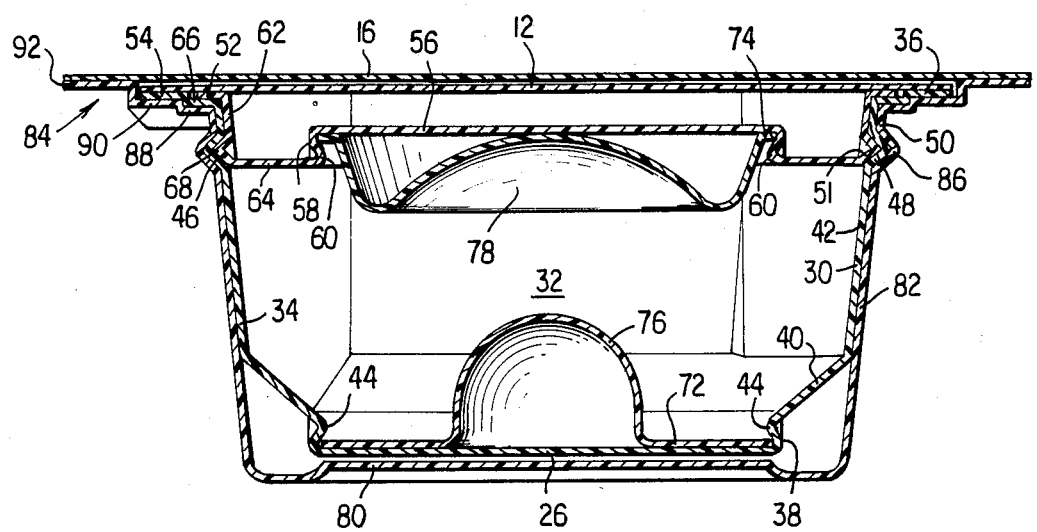
FIG. 4 is a transverse cross sectional view taken on the line 4—4 of FIG. 3.
Figure 5:
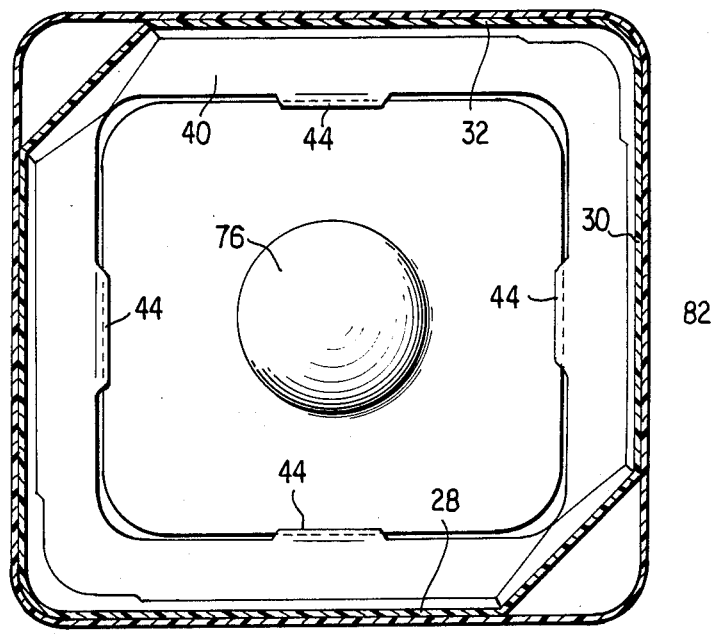
FIG. 5 is a horizontal cross sectional view taken on the line 5—of FIG. 2.

The lid 22 has a central wall portion 56 which, preferably, is of the same size and configuration as the container bottom wall 26, short, downwardly extending vertical wall portions 58 bounding the central portion and provided with inwardly projecting lugs 60 spaced downwardly by a short distance from the central wall portion, outer vertical wall portions 62, a horizontal wall portion 64 extending between the inner and outer vertical portions, and an outwardly projecting lip 66. The outer wall portions are closely received within the upper wall sections 42 of the container 18 and are provided with outwardly projecting lugs 68 of complementary configuration to the recesses 51. The lip 66 of the lid is of such size as to overly the inner horizontal zone 52 of the container lip 36. As can be seen from FIG. 3, the plan configuration of the lid 18 is substantially that of the upper end of the container 18 with the exception that one corner 70 of the lid is cut back to provide a finger access to assist in removal of the lid from the container.

Each of the inserts 20 and 24 has a planar base portion 72, 74, respectively, which is of the same configuration and slightly smaller that the bottom wall 26 of the container or the central wall portion 56 of the lid. Centrally located on the base portion of each insert is a projection which may be convex, as is the case of the projection 76 of the insert 20, or concave with bounding side walls, such as the projection 78 of the insert 24. As will be described in greater detail below, these projections are configured so as to together provide cradling for the item contained in the package. The insert 20 is intended to be snapped into the container 18, being retained against the bottom wall portion 26 thereof by the lugs 44 while insert 24 is retained in the lid against the wall portion 56 by the lugs 60.

Figure 6:
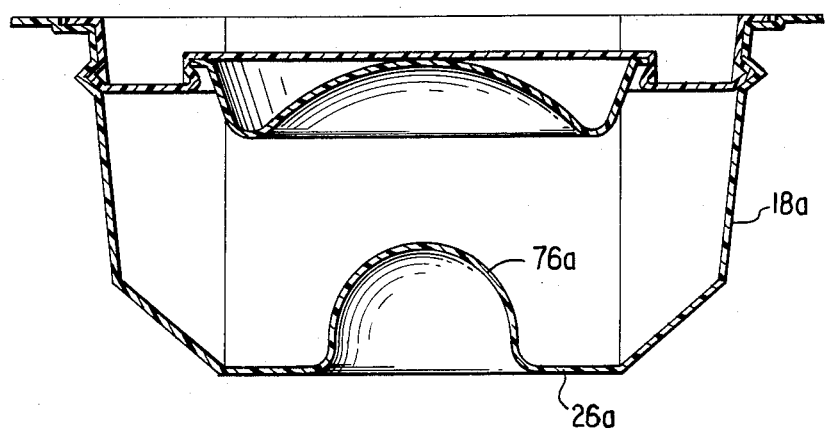
FIGS. 6 and 7 are transverse cross sectional views of alternate forms of the inner container and lid.
Figure 7:
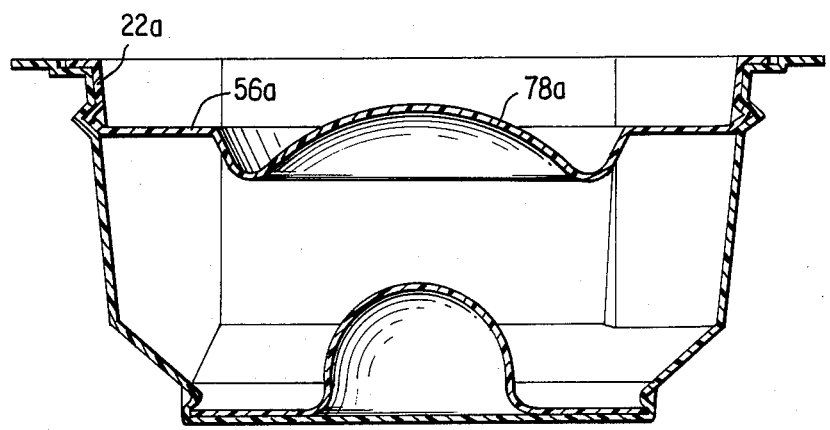

As is shown in FIGS. 6 and 7, either the inner container bottom wall or the lid may include an integrally formed projection with the other of these carrying an insert. The container 18a of FIG. 6, for example, is provided on its bottom wall 26a with an upwardly extending projection 76a while the lid of this package configuration is of the type described above. Alternatively, as is shown in FIG. 7, the lid 22a includes a downwardly extending projection 78a formed integrally with the central wall portion 56a while the inner container carries an insert as previously described.

The outer package 14 is again an open-top container having a bottom wall 80, upwardly extending side walls 82 and an outwardly projecting lip 84. Each of the side walls 82 is provided, adjacent the upper end thereof, with an outwardly projecting recess 86 of complementary configuration to the lugs 46 of the inner container side walls. The outer package lip 84 is doubly stepped, having inner, intermediate and outer horizontal zones 88, 90 and 92, respectively. Two opposite corners 94 of the lip may be recessed to provide access regions for removal of the inner package.

Preferably, each of the inner and outer packages, the lid and the inserts are manufactured of thermoformed plastic materials. Any suitable inert, sterilizable material may be employed. Suitable materials include polyethylene and polyesters.

The packaging of an item such as a hip joint prosthesis involves the selection of appropriate ones of the inserts 20 and 24 to securely cradle the item, it will be understood that a number of inserts having different sized projections are provided in accordance with the range of sizes of items to be packaged. The appropriate inserts are snapped into position in the inner package container 18 and the inner package lip 22, being retained in place, as described above, by the corresponding lugs. With the item in place in the inner package, the lid in placed thereon, the lugs 60 of the lid engaging the recesses 51 of the container side walls to retain the lid in position. A first plastic film cover 12 is bonded to the outer horizontal surface 50 of the inner package lip 36 to seal this package. The film cover is of a material which is impervious to bacteria but pervious to sterilizing agents such as ethylene oxide. Spun bonded polyethylene film (such as that sold under the trademark TYVEK, a Dupont product) is a suitable material. Following sterilization of the sealed inner package and its contents, this assembly is placed in the outer package 14, the outwardly projecting lugs 46 of the inner package engaging the corresponding recesses 86 of the outer container side walls to retain the inner package in position. A second plastic film cover 16, preferably of the same material as the inner cover 12, is bonded to the outermost zone 90 of the outer package lip 84 and the complete assembly again sterilized. The recessed corners 94 of the outer container lip, the opposite angled corners of the inner package and the angled intermediate wall portions of the inner package provide passages to facilitate the flow of the sterilizing gas fully around the inner package to assure complete sterilization.

In the preparation for the use of the packaged item in surgury, the outer cover 14 is removed and the sealed inner package removed from the outer container. As the inner package remains sealed until opened during the surgical procedure, the sterility of the item is assured.

By virtue of the interlocking relationships between the inserts and the inner package and lid and those between the two packages, secure packaging of the item is achieved. The double wall configuration of the overall package also contributes to the strength of the packaging.

As only the inserts 20 and 24 need be changed to accomodate any of a wide range of different size or different configuration items, the package arrangement of the present invention permits a substantial reduction in package inventory which must be maintained by the item manufacturer. Also, as the package configuration is not varied, the need for obtaining separate regulatory approval for each package is reduced substantially if not totally eliminated.

While a preferred embodiment of the invention has been illustrated and described in detail herein, it will be understood that changes and additions may be had therein and thereto without departing from the spirit of the invention. Reference should, accordingly, be had to the appended claims in determining the true scope of the invention.

I claim:

1. A package for holding a medical item such as a prosthesis part comprising:
   a container having a bottom and side walls, each side wall having first, inwardly projecting lugs closely spaced from said bottom wall and second, outwardly projecting lugs and complementary recesses adjacent the upper end thereof;
   a lid for said container, said lid having outer side walls closely receivable within said side walls of said container and including outwardly projecting lugs adapted to mate with said recesses, inner side walls spaced from said outer side walls, a top wall, and inwardly projecting lugs on said inner side walls closely adjacent said top wall;

a first insert having a planar base portion of substantially the same configuration as said container bottom wall and an upwardly projecting central portion, said insert being adapted to be retained in said container between said bottom wall and said first lugs thereof; and a second insert having a planar base portion of substantially the same configuration as said top wall of said lid and a downwardly projecting central portion, said second insert being adapted to be retained in said lid between said top wall and said inwardly projecting lugs thereof;

the arrangement being such that said projections of said first and second inserts, when said inserts are retained in said container and said lid, respectively, and said lid is positioned on said container, engage opposite sides of the item and retain the same in position.

2. The package of claim 1 wherein each said side wall of said container includes a lower, vertical wall portion extending upwardly from said bottom wall and having said first lugs thereon and an upper, diverging wall portion.

3. The package of claim 2 wherein said bottom wall of said container and said top wall of said lid are of the same plan configuration.

4. The package of claim 2 wherein said container has an outwardly projecting lip at the upper end of said side walls and said package further includes a film cover sealed to said lip.

5. The package of claim 4 further including a second container having a bottom and side walls and of such size as to closely receive said firstmentioned container, said side walls of said second container having recessed portions adapted to engage said second lugs of said firstmentioned container, said second container also having an outwardly projecting lip at the upper end of said side walls thereof, and said package further including a second film cover sealed to said lastmentioned lip and overlying said first film cover.

6. The package of claim 5 wherein each of said film covers is impervious to bacteria but pervious to sterilizing agents.

7. The package of claim 5 wherein said lip of said second container includes an inner lip portion adapted to receive said lip of said firstmentioned container and an outer lip portion stepped upwardly from said first lip portion.

8. A package for holding a medical item such as a prosthesis part comprising:

an inner container having a bottom and side walls, each side wall having first, inwardly projecting lugs closely spaced to said bottom wall and second, outwardly projecting lugs and complementary recesses adjacent the upper end thereof;

a lid for said container, said lid having outer side walls closely receivable within the side walls of said inner container and including outwardly projecting lugs adapted to mate with said recesses, inner side walls spaced from said outer side walls, a top wall, and inwardly projecting lugs on said inner side walls closely adjacent said top wall;

a first insert having a planar base portion of substantially the same configuration as said inner container bottom wall and an upwardly projecting central portion, said insert being adapted to be retained in said inner container between said bottom wall and said first lugs thereof;

a second insert having a planar base portion of substantially the same configuration as said top wall of said lid and a downwardly projecting central portion, said second insert being adapted to be retained in said lid between said top wall and said inwardly projecting lugs; and an outer container having a bottom wall and side walls and of such size as to closely receive said inner container, said side walls of said outer container having recessed portions adapted to engage said second lugs of said inner container.

9. The package of claim 8 further including a first plastic film cover for sealing said inner container and said lid and a second plastic film cover for sealing said second container.

10. A package for holding a medical item such as a joint prosthesis comprising:

a container having bottom and side walls, each side wall having inwardly projecting lugs closely spaced from said bottom wall;

a lid for said container, said lid having a top wall and side walls, said side walls being closely receivable within said container and including inwardly projecting lugs closely spaced from said top wall;

a first insert having a planar base portion of substantially the same configuration as said container bottom wall and an upwardly projecting central portion, said insert being adapted to be retained in said container between said bottom wall and said lugs thereof; and a second insert having a planar base portion of substantially the same configuration as said top wall of said lid and a downwardly projecting central portion, said second insert being adapted to be retained in said lid between said top wall and said lugs thereof;

the arrangement being such that said projections of said first and second inserts, when said inserts are retained in said container and said lid, respectively, and said lid is positioned on said container, engage opposite sides of the item and retain the same in position.

11. The package of claim 10 wherein said bottom wall of said container and said top wall of said lid are of the same configuration.

12. The package of claim 10 further including a second container having bottom and side walls and of such size as to closely receive said firstmentioned container.

13. The package of claim 12 further including a first film cover adapted to seal said firstmentioned container and said lid and a second film cover adapted to seal said second container.

14. The package of claim 12 wherein said side walls of said lid, said firstmentioned container and said second container are each provided with interengaging lugs and recesses whereby said lid and said containers interlock forming a secure package assembly.

15. A package for holding a medical item such as a prosthesis part comprising:

an inner container having a bottom and side walls, each side wall having first, outwardly projecting lugs and complementary recesses adjacent the upper end thereof;

a lid for said container, said lid having outer side walls closely receivable within the side walls of said container and including outwardly projecting lugs adapted to mate with said recesses and a top wall;

one of said inner container bottom wall and said lid top wall having an integrally formed projection extending inwardly, the other of said inner container and said lid having additional, inwardly projecting lugs on the side wall thereof closely adjacent the corresponding bottom or top wall; and an insert having a planar base portion of substantially the same configuration as said corresponding wall and including a projecting center portion, said insert being adapted to be retained between said additional lugs and said corresponding wall.

16. The package of claim 15 further including a second container having bottom and side walls and of such size as to closely receive said firstmentioned container.

* * * * *